(12) United States Patent
Laseur et al.

(10) Patent No.: US 11,679,176 B2
(45) Date of Patent: Jun. 20, 2023

(54) METHOD AND SYSTEM FOR LED BASED VIRUS AND BACTERIA REMOVAL

(71) Applicant: Jibe Lighting North America Limited Liability Company, Parkland, FL (US)

(72) Inventors: Lucien Laseur, Hoevelaken (NL); Todd Darling, Parkland, FL (US); Mehron Massoud Talebi, Parkland, FL (US)

(73) Assignee: Jibe Lighting North America Limited Liability Company, Parkland, FL (US)

( * ) Notice: Subject to any disclaimer, the term of this patent is extended or adjusted under 35 U.S.C. 154(b) by 306 days.

(21) Appl. No.: 17/033,646

(22) Filed: Sep. 25, 2020

(65) Prior Publication Data

US 2022/0096702 A1    Mar. 31, 2022

(51) Int. Cl.
| | |
|---|---|
| *A61L 9/20* | (2006.01) |
| *A61L 9/22* | (2006.01) |
| *B01D 46/00* | (2022.01) |
| *F21V 33/00* | (2006.01) |
| *F21Y 115/10* | (2016.01) |

(52) U.S. Cl.
CPC ............... *A61L 9/205* (2013.01); *A61L 9/22* (2013.01); *B01D 46/0028* (2013.01); *F21V 33/0096* (2013.01); *A61L 2209/12* (2013.01); *A61L 2209/14* (2013.01); *A61L 2209/16* (2013.01); *A61L 2400/12* (2013.01); *B01D 2255/20707* (2013.01); *B01D 2255/802* (2013.01); *F21Y 2115/10* (2016.08)

(58) Field of Classification Search
CPC .......... B01D 46/0028; A61L 9/22; A61L 9/20
See application file for complete search history.

(56) References Cited

U.S. PATENT DOCUMENTS

| | | | |
|---|---|---|---|
| 7,228,429 B2 | 6/2007 | Monroe | |
| 7,265,669 B2 | 9/2007 | Call | |
| 8,168,122 B2 | 5/2012 | Lee | |
| 8,630,820 B2 | 1/2014 | Amis | |
| 9,393,338 B2 | 7/2016 | Livchak et al. | |
| 9,443,415 B2 | 9/2016 | Nepo | |
| 9,715,242 B2 | 7/2017 | Pillai et al. | |
| 10,510,219 B1 | 12/2019 | Zalewski et al. | |
| 2005/0189210 A1* | 9/2005 | Uslenghi | A61L 9/20 422/186.3 |
| 2010/0307332 A1* | 12/2010 | Yuen | B03C 3/383 96/25 |
| 2011/0030560 A1* | 2/2011 | Bohlen | A61L 9/22 96/57 |
| 2017/0246329 A1 | 8/2017 | Lloyd | |
| 2018/0322405 A1 | 11/2018 | Fadell et al. | |

* cited by examiner

*Primary Examiner* — Kevin Joyner
(74) *Attorney, Agent, or Firm* — Pablo Meles

(57) ABSTRACT

A system (10) for removing airborne pathogens can include a housing (1, 4, and 6) having at least one or more chambers, a bipolar ionizer (9A), at least one particle filter (8), and an ultra violet light radiation source (5A) residing in at least one or more chambers. Furthermore, the embodiments can include the use of a ventilation system which can include a fan (3) that draws in surrounding air at an intake (7A) and directs the surrounding air towards the at least one particle filter, the bipolar ionizer, and the ultra violet light radiation source before the ventilation system expels the surrounding air drawn through the intake through an exhaust vent (7B).

20 Claims, 6 Drawing Sheets

10

10

10

10

10

200

METHOD AND SYSTEM FOR LED BASED VIRUS AND BACTERIA REMOVAL

CROSS-REFERENCE TO RELATED APPLICATIONS

Not applicable

BACKGROUND

The present disclosure is directed to a method, apparatus and system for aiding in the performance of killing or neutralizing viruses and bacteria or other pathogens.

DESCRIPTION OF THE RELATED ART

Current methods and systems addressing some of the issues resolved by the current embodiments use devices that kill airborne viruses, but are generally unsafe for humans and animals that are present within the proximity of the devices. Some devices use a timer or motion detectors, but still do nothing to protect the incidental activation during the presence of humans or mammals despite some of the safety features such as timers and motion detectors. Some existing systems fail to provide an extreme high percentage of neutralizing the known pathogens.

SUMMARY

In some embodiments, a system for removing airborne pathogens can include a housing having at least one or more chambers, a bipolar ionizer residing in at least one or more chambers, at least one particle filter residing in at least one or more chambers, and an ultra violet light radiation source residing in at least one or more chambers. Furthermore, the embodiments can include the use of a ventilation system that draws in surrounding air at an intake and directs the surrounding air towards the at least one particle filter, the bipolar ionizer, and the ultra violet light radiation source before the ventilation system expels the surrounding air drawn through the intake through an exhaust vent.

In some embodiments, the bipolar ionizer is of high voltage and low amperage sufficient to rip apart airborne pathogens including viruses and bacteria. In some embodiments, the at least one particle filter can be a carbon filter or a HEPA filter and in other embodiments the particle filter can further include a nano-coating that is photo-catalytic such as a nano-coating of titanium oxide. In some embodiments, the ultra violet light radiation source includes a source of at least one or more of UV-A, UV-B, or UV-C radiation. In some embodiments, the UV light source can interact with the nano-coating to further eliminate or kill pathogens as part of an overall system. In some embodiments, the system is a portion of a light emitting diode lighting fixture that includes light emitting diodes that emit light in the visible spectrum. In some embodiments, the system includes a housing configured to keep the one or more of UV-A, UV-B, or UV-C radiation limited to an internal portion of the housing and thereby preventing mammalian exposure external to the housing.

In some embodiments, the at least one particle filter includes a first particle filter adjacent to the bipolar ionizer. In some embodiments, the system further includes at least a second particle filter adjacent to the exhaust vent. The system is not limited as to the number particle filters used. In some embodiments, the ventilation system includes a turbo fan or centrifugal fan. In some other embodiments, the ventilation system includes a structure that utilizes external fans enabling the intake of surrounding air and expelling of processed air. In some embodiments, the system includes a directional airflow frame that helps direct the airflow in and out of the system. In some embodiments, the bottom side of the airflow frame is treated or coated with a nano-coating that is a photo catalyst such as titanium dioxide that can be energized by UV radiation source or UV light. In some embodiments, the UV radiation source is of a particular wavelength or frequency. In some embodiments, a chamber with the UV light source (such as UV-A, UV-B, or UV-C) further includes reflective materials that help diffuse the UV light source within such chamber or chambers.

In some embodiments the at least one particle filter is treated with a photo catalyst (such as a titanium dioxide nano-coating that is continuously energized by a UV-A, UV-B, or UV-C light source that forms part of the ultra violet light radiation source) that causes anti-microbial activity.

In some embodiments, the system is an LED lighting fixture including a system for removing airborne pathogens that includes a housing, a bipolar ionizer residing in the housing, at least a first particle filter residing in the proximity of the bipolar ionizer within the housing, and an ultra violet light radiation source residing in the proximity of the first particle filter within the housing. The LED lighting fixture can further include a ventilation system that draws in at an intake surrounding air surrounding the LED lighting fixture and directs the surrounding air towards at least the first particle filter, the bipolar ionizer, and by the ultra violet light radiation source before expelling the treated surrounding air drawn through the intake out through an exhaust vent.

In some embodiments, the first particle filter further includes a coating of titanium oxide or other photo-catalyst material that reacts to exposure to ultraviolet light. In some embodiments, the ultra violet light radiation source includes a source of UV-A radiation and in some embodiment the housing is configured to keep the UV-A radiation limited to an internal portion of the housing to prevent external exposure of UV-A radiation outside the housing. In some embodiments, the LED lighting fixture includes a second particle filter in proximity to exhaust vent. In some embodiments, a structure of the LED lighting fixture includes the housing having a top cover, a directional airflow frame, the LED light panel, and a lower frame and an area encompassed by the directional airflow frame, the LED light panel, and the lower frame forms a treatment chamber where air is treated by the UV light source and a photo-catalyst material that is nano-coated within the treatment chamber.

In some embodiments, an LED lighting fixture including a system for removing airborne pathogens includes a housing having an intake where surrounding air is drawn in and an exhaust vent where the surrounding air that is drawn in is drawn out, a bipolar ionizer residing in the housing, at least a first particle filter residing in the proximity of the bipolar ionizer within the housing, an ultra violet light radiation source residing in the proximity of the first particle filter within the housing, and at least one fan for drawing in at the intake surrounding air surrounding the LED lighting fixture and directing the drawn-in surrounding air towards the first particle filter, the bipolar ionizer, and by the ultra violet light radiation source before expelling the drawn-in surrounding air through the exhaust vent.

In some embodiments, the first particle filter is treated with a photo catalyst in a form of a titanium dioxide nano-coating that is continuously energized by the ultra violet radiation source. In some embodiments, the LED lighting fixture further comprises at least a second particle filter residing in the proximity of other intake vents and/or one or more exhaust vents. In some embodiments, the first particle filter and the second particle filter or additional particle filters can be treated with a titanium dioxide nano-coating that is continuously energized by the ultra violet radiation source.

DETAILED DESCRIPTION

Economies, governments, and social systems including schools are all built for operation in the presence of people. As evidenced by the rapid spread of SARS-CoV-2, lack of preparedness leads to systemic failure. The embodiments disclosed herein are engineered with a highly advanced and seamless system capable of being integrated into existing infrastructure. Use of the various embodiments herein will ultimately lead to disease preparedness for today and for the distant future.

More particularly, airborne pathogens such as tuberculosis, influenza, & SARS-CoV-2 pose a major issue to the safety and productivity of the public. With increasingly globalized economies as well as a rise in demand for mass transport systems, airborne pathogens are presented with an unparalleled opportunity to cause uncontrollably rapid outbreaks. Existing temporary solutions only provide expensive and wasteful temporary protection.

The most durable protections are implemented as passive, infrastructure-based measures. Areas of physical gathering should be built to continuously protect those within both physically and medically. Lighting is generally a ubiquitous part of an infrastructure-based solution and various embodiments herein using modified lighting and specialized coatings provide a durable, multifaceted solution for active disease protection. The various embodiments can utilize an energy efficient LED light panel with a safe, integrated air sterilization system. Additionally, some embodiments can further use an FDA & EPA approved surface nano-coating built to continuously neutralize surface pathogens and effectively halt the spread of disease. Other embodiments can still retain the form factor of a light panel, but not necessarily include visible LED light panel itself if visible light is not a requirement of the overall system.

The embodiments are also flexible in terms of the types of places they can be implemented in and in terms of the types of apparatus or system form factors. The embodiments herein can be implemented in form factors to retrofit existing lighting fixtures or in wholly new designs that mimic light fixtures or other fixtures or structures. For example, the embodiments can be implemented in long term standing structures within commercial, retail, medical, schooling, and governmental facilities or even within vehicles or ships such as buses, subways, trains, airplanes or cruise ships to name a few. In some embodiments, the system can be implemented as part of or be integrated with a central HVAC system or other air conditioning or air ventilation system.

Figure 1A:
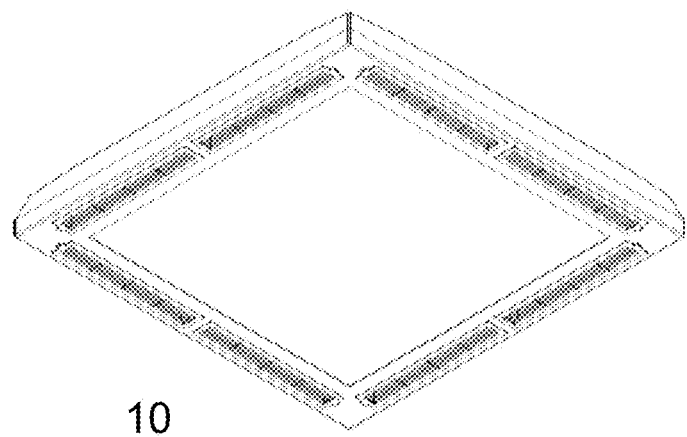
FIG. 1A illustrates a front or bottom perspective view of a system or apparatus for LED based virus and bacteria removal in accordance with the embodiments.
Figure 1C:
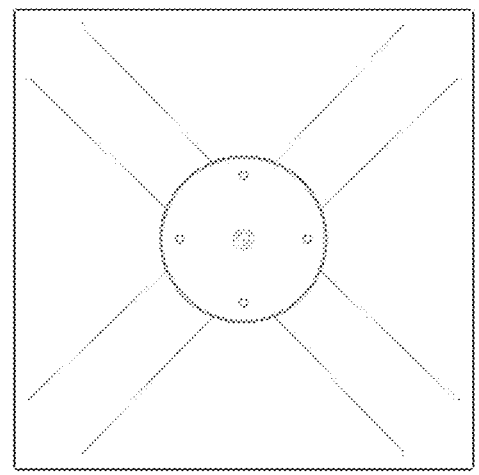
FIG. 1C is a rear or top elevation view of the system or apparatus of FIG. 1A.
Figure 1B:
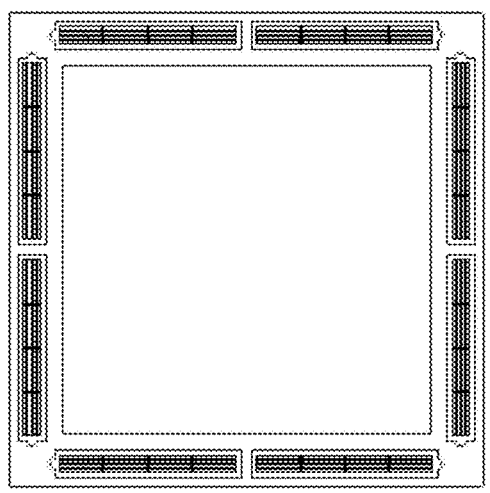
FIG. 1B is a front or bottom elevation view of the system or apparatus of FIG. 1A.
Figure 1D:
FIG. 1D is a side elevation view of the system or apparatus of FIG. 1A.

Referring to FIGS. 1A-1D, several external views are illustrated of an exemplary system 10 for removing airborne pathogens. FIG. 1A illustrates a perspective bottom or front view of the system 10 in the form factor of a light fixture. FIG. 1B depicts an elevational view of the bottom or front of the system 10. FIG. 1 illustrates a top or rear view of the system 10 and FIG. 1D illustrates a side view of the system 10 where all 4 sides of the system 10 will generally look the same.

Figure 1E:
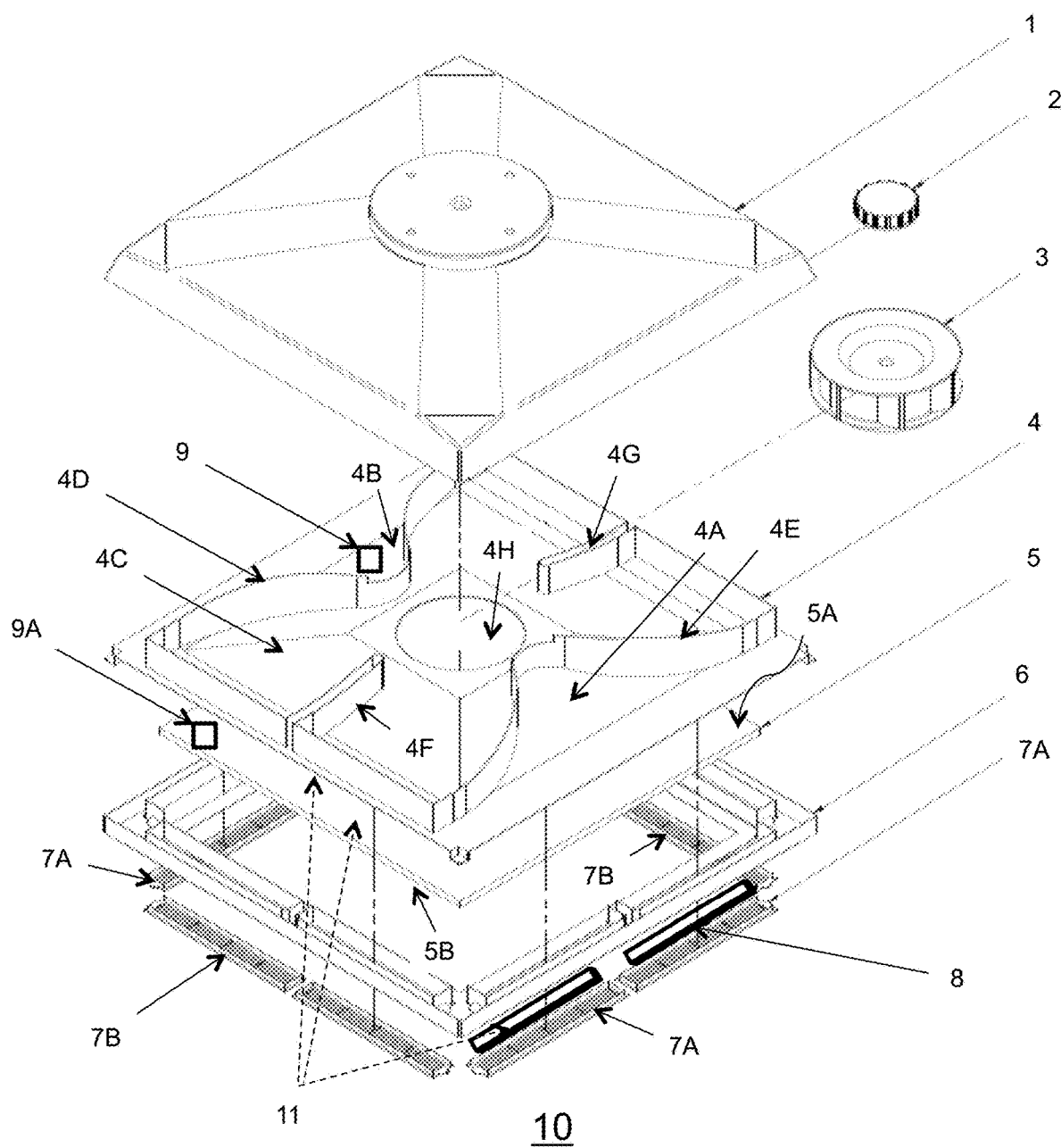
FIG. 1E is an exploded view of the system or apparatus of FIG. 1A in accordance with the embodiments.

Referring to FIG. 1E, an exploded view of the system 10 more clearly depicts the structure and components of system including a housing formed by a top cover 1, a directional airflow e 4, an LED light panel 5, and a lower frame 6. Configured in between the top cover 1 and the directional airflow frame 4 is a motor 2 that drives a centrifugal fan 3 as well as a controller board 9 that can control the electrical components of the system including the motor 2 and the lights or LEDs within or forming part of the LED light panel 5. The motor is typically a DC motor, but can also be an AC motor in certain embodiments. In some embodiments, particularly where the motor or fan is not used, rechargeable batteries can be used to power the system 10. The rechargeable batteries can be recharged using external power sources or powered with generated power from a wind or airflow driven turbine. The controller board 9 can also control and power the bipolar ionizer 9A that can reside within the treatment chamber where other processing of the air takes place. In some embodiments bipolar ionizer 9A can reside on the top surface (5A) of the LED light panel 5 and can include one or ionizers. In one particular embodiment, the bipolar ionizer 9A can include 2 ionizers and 4 cable pairs. In other embodiments, the ionizers can reside elsewhere within system 10 and can include one or more ionizers.

In some embodiments, the directional airflow frame 4 includes several walls that chambers when the airflow frame 4 is mated with the top cover 1. More particularly, the wall 4E when mated with the top cover 1 forms the chamber 4A and a portion of a chamber 4C. The wall 4D when mated with the top cover 1 forms the chamber 4B and a portion of the chamber 4C. Walls 4F and 4G when mated with the top cover 1 further form the chamber 4C. In the center of chamber 4C is a central access hole or aperture 4H where treated air is drawn out of a treatment chamber underneath the directional airflow frame (using the centrifugal fan 3) and into the chamber 4C and further expelled out of exhaust vents 7B. In this embodiment, the chamber 4C is in the shape of an "X" and efficiently helps air flow into and out of the chamber 4C. Other shapes or patterns can be used to efficiently create airflow based on the application.

Further note that the bottom area of the top cover 1 can include structures such as beads of silicone or other materials that help mate with the walls 4D, 4E, 4F, and 4G to form the chambers (4A, 4B, and 4C) as needed. Further note that the LED panel 5 can include UV radiation sources such as UV-A, UV-B, or UV-C on a top surface 5A of the panel 5 and visible LED lights on a bottom surface 5B of the panel 5. Also note that the bottom area of the direction airflow frame 4 can be coated with a photo-catalytic nano-coating 11 (such as titanium oxide (TiO2) or silver ion or other compounds or materials) that reacts with UV light to further enhance the effectiveness of the elimination of pathogens. The bottom area of the directional airflow frame 4 can also include reflective materials that help diffuse the UV radiation source coming from the top surface 5B of the panel 5. Portions of the top surface 5A of panel 5B can also include reflective materials and/or photo-catalytic nano-coating 11 where a treatment chamber is formed between the bottom frame 6, the top surface 5A of the LED light panel 5, and the bottom surface of the directional airflow frame 4. In some embodiments where a nano-coating of TiO2 is used, a 254 nm UV-C radiation source is specifically used to recharge the TiO2 when natural UV-C is not sufficient to keep the TiO2 at an optimal antimicrobial performance level.

The bottom frame 6 can include slots for the intake vents 7A and exhaust vents 7B. In some embodiments, the intake vents 7A can be configured to receive particle filters 8 that can be carbon filters, HEPA filters or other filters that are suitable for a particular configuration. The exhaust vents 7B can optionally also use and receive particle filters 8, but most embodiments may not require further filtering as the intake filters 8, bipolar ionization and photo-catalytic treatment will generally treat the surrounding air to remove the vast majority, if not all of the airborne pathogens coming through the intake vent 7A. Furthermore, not having a particle filter at the exhaust vent 7B will likely provide better airflow out of the system 10 in most embodiments. Notwithstanding, systems that require additional levels of cleaning can include such additional filtering at the exhaust vents. In addition to the nano-coating on the surface of the treatment chamber as described above, some embodiments can further include nano-coating on the surface of the particle filters 8. In some embodiments, the slats of the intake vents 7A can be directed away from the slats of the exhaust vents 7B so that the system 10 avoids re-circulating air merely adjacent to the area around the system 10.

Figure 2:
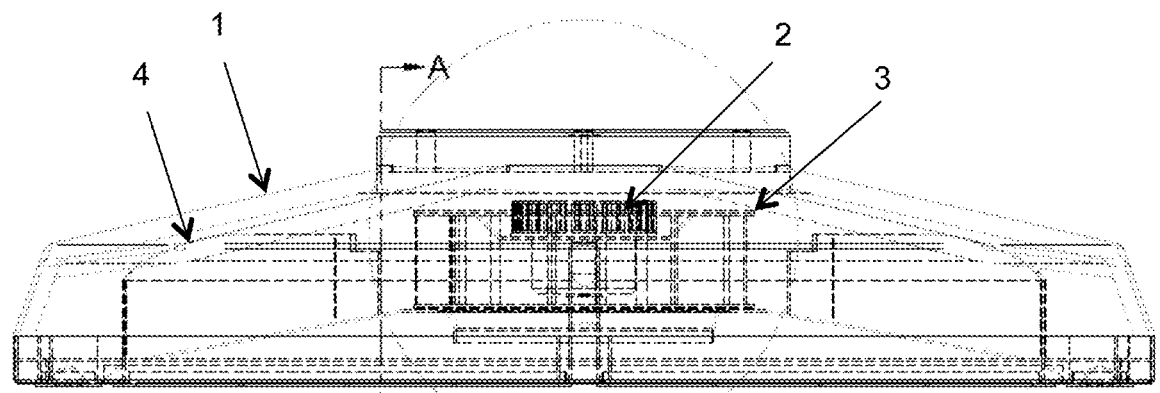
FIG. 2 illustrates an internal side view of system of FIG. 1A in accordance with the embodiments.
Figure 3:
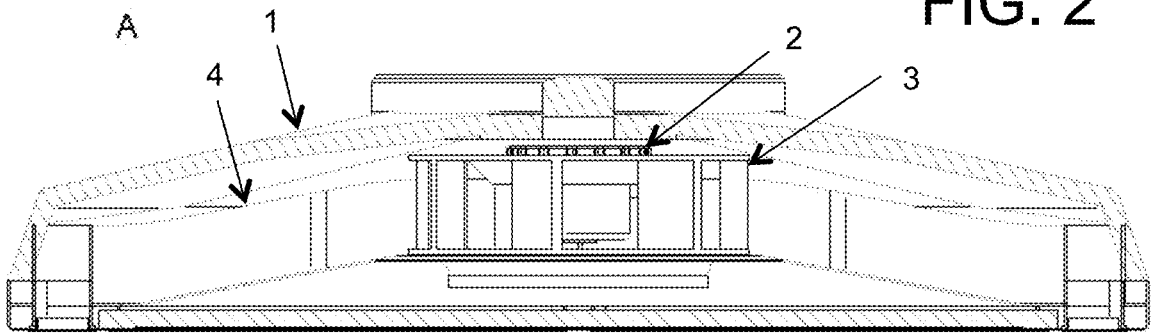
FIG. 3 illustrates another side view from the perspective of Section A-A as designated in FIG. 2.

FIGS. 2 and 3 provide transparent and cut views of the system 10 further emphasizing the fan assembly that includes the motor 2 and centrifugal fan 3 configured between the top cover 1 and directional airflow frame 4. FIG. 3 illustrates a cut view along line A-A of FIG. 2.

In some embodiments, the system can include internal ventilators for directional airflow, LED recessed ceiling light with an inflow and outflow opening for air, where the internal ventilators includes fans that pull in surrounding air and force out pathogen-free, airborne virus-free air, and bacteria-free air.

Internally, such a system can include bipolar ionization (also sometimes referred to as plasma cluster ionization) with High voltage positive (+) and negative (−) cluster ionization to destroy and kill viruses, internal washable or replaceable particle filter or filters close to the ionization to catch ionized particles with viruses attached. As discussed above, the particle filter can also include a photo-catalyst and treated with TiO2 (titanium dioxide) nano-coating, for example, that is continuously or periodically being energized by the UV-C light which creates an anti-microbial activity that destroys and kills viruses. Again, such a system can include a UV lamp such as a UV-C or UV-A lamp that is internal and is not exposed to anything outside of the housing/frame of the system.

Figure 4:
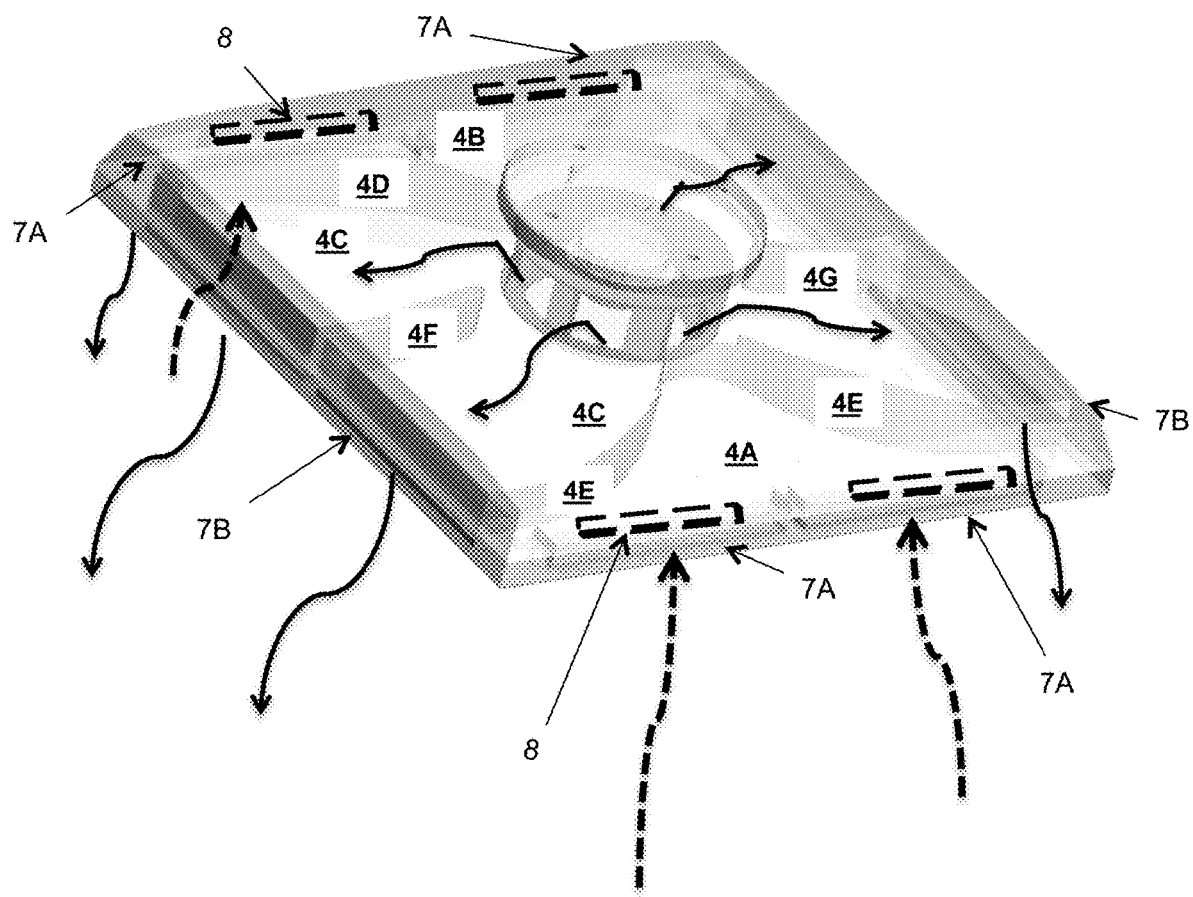
FIG. 4 is a transparent perspective view of the system or apparatus of FIG. 1A-1E illustrating an airflow pattern in accordance with the embodiments; yet another system in accordance with the embodiments.

Operationally, with respect to airflow, FIG. 4 illustrates a transparent perspective view of the system 10 with dashed arrows representing inflow directions and solid arrows representing outflow directions. With further reference to FIG. 1E and FIG. 4, ambient or surrounding air is drawn in through intake vents 7A and corresponding particle filters 8. The treatment chamber formed in an area between the bottom of the directional airflow frame 4, the top surface (5A) of the LED panel 5 and bottom frame 6 serves to treat the ambient air (after the particle filter 8) with bipolar ionization which causes pathogens to form clumps with ions and further treats such clumps and other particulates with the photo-catalytic coating 11 to further neutralize any surviving pathogens. The multi-faceted treated or processed air within the treatment chamber is then sucked through the aperture or hole 4H using the centrifugal fan (or using other techniques using negative air pressure) and directed into the various sections of the chamber 4C on the top surface of the directional airflow frame 4 as shown. The "X" shape of the directional airflow frame 4 further helps the treated air to flow out of the chamber 4C and out of the exhaust vents 7B.

In some embodiments (with reference to FIGS. 1A-E and 2-4, a system 10 for removing airborne pathogens can include a housing having at least one or more chambers (4A, 4B, 4C, and/or the treatment chamber below the directional airflow frame 4 as discussed above), a bipolar ionizer 9A residing in at least one or more chambers, at least one particle filter 8 residing in at least one or more chambers, and an ultra violet light radiation source (5A) residing in at least one or more chambers. Furthermore, the embodiments can include the use of a ventilation system that draws in surrounding air at an intake 7A and directs the surrounding air towards the at least one particle filter 8, the bipolar ionizer (9A), and the ultra violet light radiation source 5A before the ventilation system expels the surrounding air drawn through the intake through an exhaust vent 7B.

In some embodiments, the bipolar ionizer 9A is of high voltage and low amperage sufficient to rip apart airborne pathogens including viruses and bacteria. In some embodiments, the at least one particle filter 8 can be a carbon filter or a HEPA filter and in other embodiments the particle filter can further include a nano-coating 11 that is photo-catalytic such as a nano-coating of titanium oxide. In some instances, the use of a carbon filter can reduce airflow and may not be recommended for particular implementations. Some combinations of filtering and bipolar ionization can also create ozone and may not be recommended in certain scenarios. In some embodiments, the ultra violet light radiation source 5A includes a source of at least one or more of UV-A, UV-B, or UV-C radiation. In some embodiments, the UV light source 5A can interact with the nano-coating 11 to further eliminate or kill pathogens as part of an overall system. In some embodiments, the system 10 is a portion of a light emitting diode (or other) lighting fixture that includes light emitting diodes that emit light in the visible spectrum. In some embodiments, the system includes a housing configured to keep the one or more of UV-A, UV-B, or UV-C radiation limited to an internal portion of the housing and thereby preventing mammalian exposure external to the housing.

In some embodiments, the at least one particle filter 8 includes a first particle filter adjacent to the bipolar ionizer 9A. In some embodiments, the system further includes at least a second particle filter (8) adjacent to the exhaust vent 7B. The system is not limited as to the number particle filters shown. In some embodiments, the ventilation system includes a turbo fan or centrifugal fan 3. In some other embodiments, the ventilation system includes a structure that utilizes external fans or drivers of airflow enabling the intake of surrounding ("dirty") air and expelling of processed ("clean") air. In some embodiments, the system 10 includes a directional airflow frame 4 that helps direct the airflow in and out of the system 10. In some embodiments, the bottom side of the airflow frame 4 is treated or coated with a nano-coating 11 that is a photo catalyst such as titanium dioxide that can be energized by UV radiation source 5A or UV light. In some embodiments, the UV radiation source 5A is of a particular wavelength or frequency such as 254 nm wavelength. In some embodiments, a chamber with the UV light source 5A (such as UV-A, UV-B, or UV-C) further includes reflective materials that help diffuse the UV light source within such chamber or chambers.

In some embodiments the at least one particle filter 8 is treated with a photo catalyst 11 (such as a titanium dioxide nano-coating that is continuously energized by a UV-A, UV-B, or UV-C light source that forms part of the ultra violet light radiation source 5A) that causes anti-microbial activity.

In some embodiments, the system is an LED lighting fixture including a system 10 for removing airborne pathogens that includes a housing (1, 4, 5, and 6), a bipolar ionizer 9A residing in the housing, at least a first particle filter 8 residing in the proximity of the bipolar ionizer 9A within the housing, and an ultra violet light radiation source 5A residing in the proximity of the first particle filter within the housing. The LED lighting fixture can further include a ventilation system that draws in at an intake 7A surrounding air surrounding the LED lighting fixture and directs the surrounding air towards at least the first particle filter 8, the bipolar ionizer 9A, and by the ultra violet light radiation source 5A before expelling the treated surrounding air drawn through the intake 7A out through an exhaust vent 7B.

In some embodiments, the first particle filter 8 further includes a coating 11 of titanium oxide or other photocatalyst material that reacts to exposure to ultraviolet light. In some embodiments, the ultra violet light radiation source 5A includes a source of UV-A radiation and in some embodiments the housing is configured to keep the UV-A radiation limited to an internal portion of the housing to prevent external exposure of UV-A radiation outside the housing. In some embodiments, the LED lighting fixture includes a second particle filter 8 in proximity to exhaust vent 7B. In some embodiments, a structure of the LED lighting fixture includes the housing having a top cover 1, a directional airflow frame 4, the LED light panel 5, and a lower frame 6 and an area encompassed by the directional airflow frame, the LED light panel, and the lower frame forms a treatment chamber where air is treated by the UV light source 5A and a photo-catalyst material 11 that is nano-coated within the treatment chamber.

In some embodiments, an LED lighting fixture including a system 10 for removing airborne pathogens includes a housing having an intake 7A where surrounding air is drawn in and an exhaust vent 7B where the surrounding air that is drawn in is drawn out, a bipolar ionizer 9A residing in the housing, at least a first particle filter 8 residing in the proximity of the bipolar ionizer 9A within the housing, an ultra violet light radiation source 5A residing in the proximity of the first particle filter 8 within the housing, and at least one fan 3 for drawing in at the intake 7A surrounding air surrounding the LED lighting fixture and directing the drawn-in surrounding air towards the first particle filter 8, the bipolar ionizer 9A, and by the ultra violet light radiation source 5A before expelling the drawn-in surrounding air through the exhaust vent 7B.

In some embodiments, the first particle filter 8 is treated with a photo catalyst in a form of a titanium dioxide nano-coating 11 that is continuously energized by the ultra violet radiation source 5A. In some embodiments, the LED lighting fixture further comprises at least a second particle filter 8 residing in the proximity of other intake vents 7A and/or one or more exhaust vents 7B. In some embodiments, the first particle filter and the second particle filter or additional particle filters 8 can be treated with a titanium dioxide nano-coating 11 that is continuously energized by the ultra violet radiation source 5A.

The photo-catalytic nano-coating can be a highly durable compound that can be applied to various surfaces within the system 10 and can further be applied to other affiliated external surfaces such as bus interiors or other high-contact regions. It reacts safely with UV light to destroy 99.9% of surface pathogens, including SARS-CoV-2.

In terms of bipolar ionization, air is brought through an intake (7A) and bipolar ionized to neutralize airborne pathogens and to allow more effective filtration, particularly when using an integrated silver ion HEPA filter.

In some embodiments, UV-A radiations used to activate the nano-coating 11 and to continuously kill pathogens taken into the system. In other embodiments, UV-C radiation might be more effective. The nano-coating can typically last a minimum of one year under normal use and in many cases, it can last up to five years or more per application. The particle filters may need to be replaced or washed after a predetermined period of time. In some embodiments, the filters may be designed to only be effective for approximately 2160 hours. The controller board 9A can be coupled to sensors and programmed to provide reminders to replace or service such filters at the appropriate intervals.

The various embodiments within the scope of the claims can include a housing frame of multiple and varying sizes that can either be used to replace, retrofit existing lighting with or without LED lighting or can be used for new lighting installations in both stationary structures and mobile vehicles that incorporates a fan or fans that draws in surrounding air and directs the air into various "treatments" that can be done in any order in one or more chambers. The "treatments" can include a bipolar or cluster ionizer treatment which can be a high voltage (10 Watt) low amperage application, which rips apart airborne viruses and bacteria. Either before or after or in some instances concurrently the air is forced to travel through a particle filter (to remove other particles such as dust, pollen, and other contaminants which may or may not be treated with TiO2 (titanium dioxide)), and from there that air can be forced to pass a UV light whereby the UV light radiation is not exposed to mammalian cells or eyes (the protective housing keeps the UV-C (or other) radiation limited to the housing internally) and where this surrounding air is further sterilized and becomes free of COVID-19 and all other known airborne virus and pathogens, bacteria with what is now sterile, pathogen free air. Additional filtering can be done before expelling the pathogen free air out of an exhaust vent. This process continuously sterilizes and cleans the air to be free of airborne viruses and bacteria.

Figure 5:
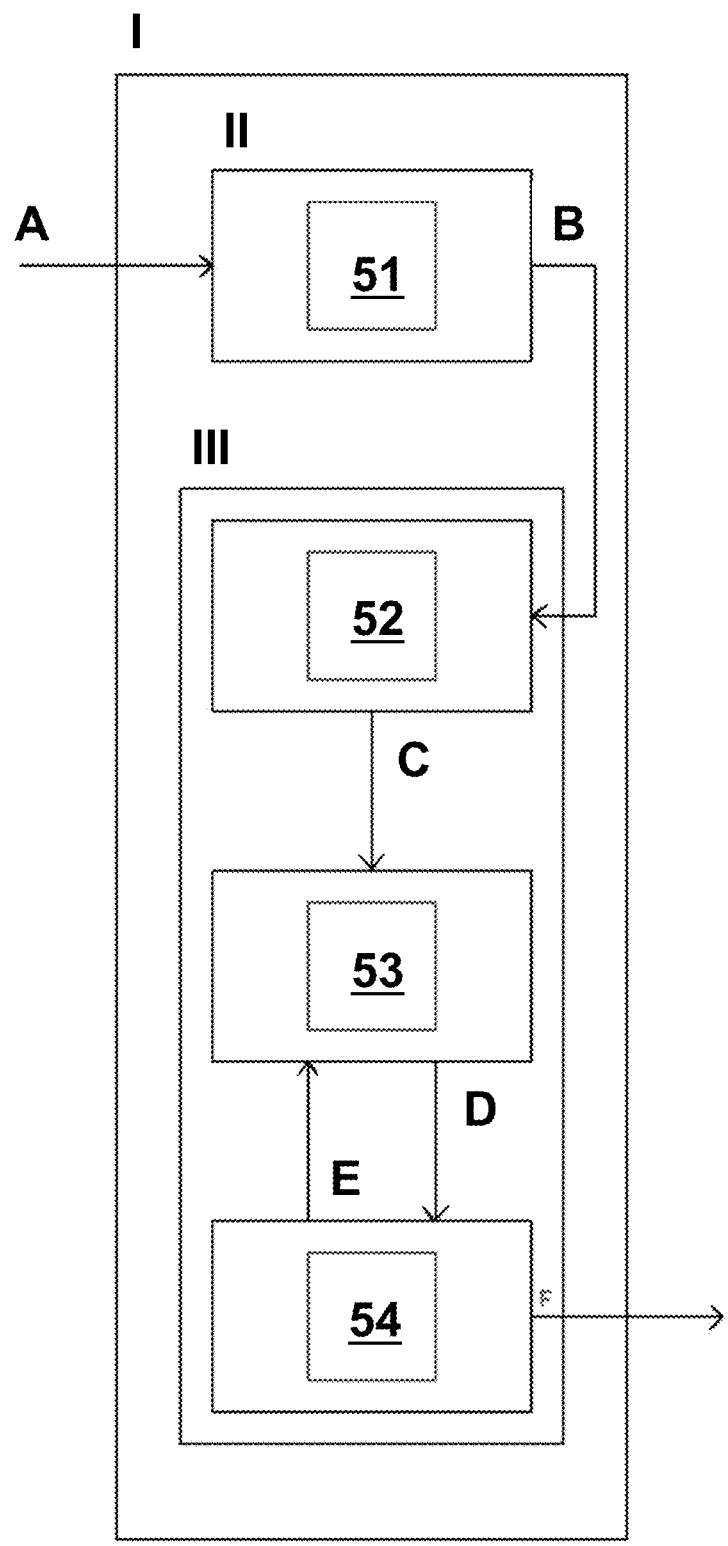
FIG. 5 is a flow chart illustrating a method in accordance with the embodiments.

FIG. 5 discloses a flow chart of a method 50 where the system 10 converts an input of a pathogen-containing gaseous fluid to a pathogen-reduced or pathogen-free gaseous fluid. Each block can represent a system component. The arrows labeled with alphabetic characters represent the flow of inputs, outputs, and intermediaries throughout the system. Arrows are shown exiting and entering components to represent the flow of inputs, outputs, and intermediaries into and out of components. The three major components of the system are labeled I, II, and III. The four major sub-components of the system are labeled with the numbers 51, 52, 53 and 54 and further note that the particular order of the components in various embodiments can be re-ordered within contemplation of the embodiments. In some embodiments, the functions of each are as follows:

Component I: A housing of a material such as metal or plastic that forms an enclosure of the system 10 which houses all components of the system 10. An electrical input is fed into the enclosure and its respective components in order to drive the flow of all processes shown. As discussed above, the electrical input can include a power source such as a battery or rechargeable battery.

Component II/Sub-Component 51: A mechanism to accelerate the flow of gaseous fluids in the surrounding air (A) to a greater velocity to be directed into the system (B). The velocity of this fluid will remain accelerated up to the exit point of the system at (F). The output (B) of this component will be directed into sub-component 52. In some embodiments, subcomponent 51 can be a fan.

Component III: A mechanism consisting of three sub-components which work in conjunction to take a gaseous, pathogen-containing fluid input (B) and output a pathogen-reduced or pathogen-free gaseous fluid (F).

Sub-Component 52: A bipolar ionization device which takes a high-velocity gaseous fluid input (B) and outputs an ionized, high velocity gaseous fluid (C) in order to develop aggregates of pathogens for facilitating pathogen removal by filtration. The output of sub-component 52 (C) is then sent to subcomponent 53.

Sub-Component 53: A particle or other filter which takes an ionized, high-velocity gaseous fluid as an input (C) and outputs a pathogen-reduced, high-velocity gaseous fluid (D). The filter can be chemically coated with titanium dioxide or other photo-catalytic coating. In order to drive the output process, an additional input of 254 nanometer ultraviolet light (or other appropriate wavelength of light) is provided (E). For example, titanium dioxide serves as a photo-catalytic medium in order to produce radical byproducts internal to sub-component 53. These radical byproducts will then react with the pathogen aggregates input by sub-component 52 to irreversibly damage pathogen reproductive abilities.

Sub-Component 54: A 254 nanometer ultraviolet light providing an catalytic output to subcomponent 53 (E) while taking a pathogen-reduced, high velocity gaseous fluid as an input (D) from sub-component 53. Remaining pathogens not reproductively inactivated by sub-component 52 are exposed to ultraviolet light to ensure full reproductive deactivation. A high-velocity pathogen-minimal gaseous fluid is then output into the surroundings (F).

In some embodiments, and with further references to FIG. 6, a system 200 can include any number and combination of the previously described components above as well as one or more processors which when executing the computer instructions, performs the functions of filtering and eliminating or killing airborne pathogens as described above.

In some embodiments, the system can utilize artificial intelligence and more particularly machine learning which can use exemplary training data and/or actual commercial use data to further refine what is intended to serve as an exemplary repetition based on a particular environment or a number of known environments. Machine learning is a method of data analysis that automates analytical model building. It is a branch of artificial intelligence based on the idea that systems can learn from data, identify patterns and make decisions with minimal human intervention. Some of the training data that can be used to help identify patterns and make decisions can include fields such as identity codes, scheduling data, location data and/or other parameters obtained from sensors such as cameras, video monitoring devices, audio devices, temperature, pressure, particulate, or other sensor data that can be programmatically configured to more adequately and accurately reflect real world conditions as a system is utilized in a particular environment and hopefully across different environments. Ideally, using machine learning enables systems to automatically learn and improve from experience without being explicitly programmed. Machine learning in the embodiments herein can focus on the development of computer programs (using the Python programming language, for example) to access data and use it to learn for itself in order to better predict when a lockbox should be in either a locked or an unlocked mode.

In some embodiments, the system can be a client device having one or more computer storage mediums containing computer instructions enabling secure access, storage, transport, and tracking of electronically tagged objects, one or more processors operationally coupled to the one or more computer storage mediums where the one or more processors perform the operations described above.

In some embodiments, the system can further include a computer-storage media coupled to a processor (or processors) and computer-executable instructions embodied in the computer-storage media that, when executed by one or more computing devices, perform a method that perform any number of steps such as performing the method of eliminating airborne pathogens using a system having LED and or UV lighting.

Various embodiments of the present disclosure can be implemented on an information processing system. The information processing system is capable of implementing and/or performing any of the functionality set forth above. Any suitably configured processing system can be used as the information processing system in embodiments of the present disclosure. The information processing system is operational with numerous other general purpose or special purpose computing system environments, networks, or configurations. Examples of well-known computing systems, environments, and/or configurations that may be suitable for use with the information processing system include, but are not limited to, personal computer systems, server computer systems, thin clients, hand-held or laptop devices, notebook computing devices, multiprocessor systems, mobile devices, microprocessor-based systems, set top boxes, programmable consumer electronics, network PCs, minicomputer systems, mainframe computer systems, Internet-enabled television, and distributed cloud computing environments that include any of the above systems or devices, and the like. As noted previously, the data processing can be any number of data processing techniques suited for tracking repetitions of a particular exercise.

For example, a user with a mobile device may be in communication with a server configured to implement the system using the aforementioned elements, according to an embodiment of the present disclosure. The mobile device can be, for example, a multi-modal wireless communication device, such as a "smart" phone, configured to store and execute mobile device applications ("apps"). Such a wireless communication device communicates with a wireless voice or data network using suitable wireless communications protocols.

The system may include, inter alia, various hardware components such as processing circuitry executing modules that may be described in the general context of computer system-executable instructions, such as program modules, being executed by the system. Generally, program modules can include routines, programs, objects, components, logic, data structures, and so on that perform particular tasks or implement particular abstract data types. The modules may be practiced in various computing environments such as conventional and distributed cloud computing environments where tasks are performed by remote processing devices that are linked through a communications network. In a distributed cloud computing environment, program modules may be located in both local and remote computer system storage media including memory storage devices. Program modules generally carry out the functions and/or methodologies of embodiments of the present disclosure, as described above.

In some embodiments, a system includes at least one memory and at least one or more processor of a computer system communicatively coupled to the at least one memory. The at least one processor can be configured to perform a method including methods described above.

According to yet another embodiment of the present disclosure, a computer readable storage medium comprises computer instructions which, responsive to being executed by one or more processors, cause the one or more processors to perform operations as described in the methods or systems above or elsewhere herein.

Figure 6:
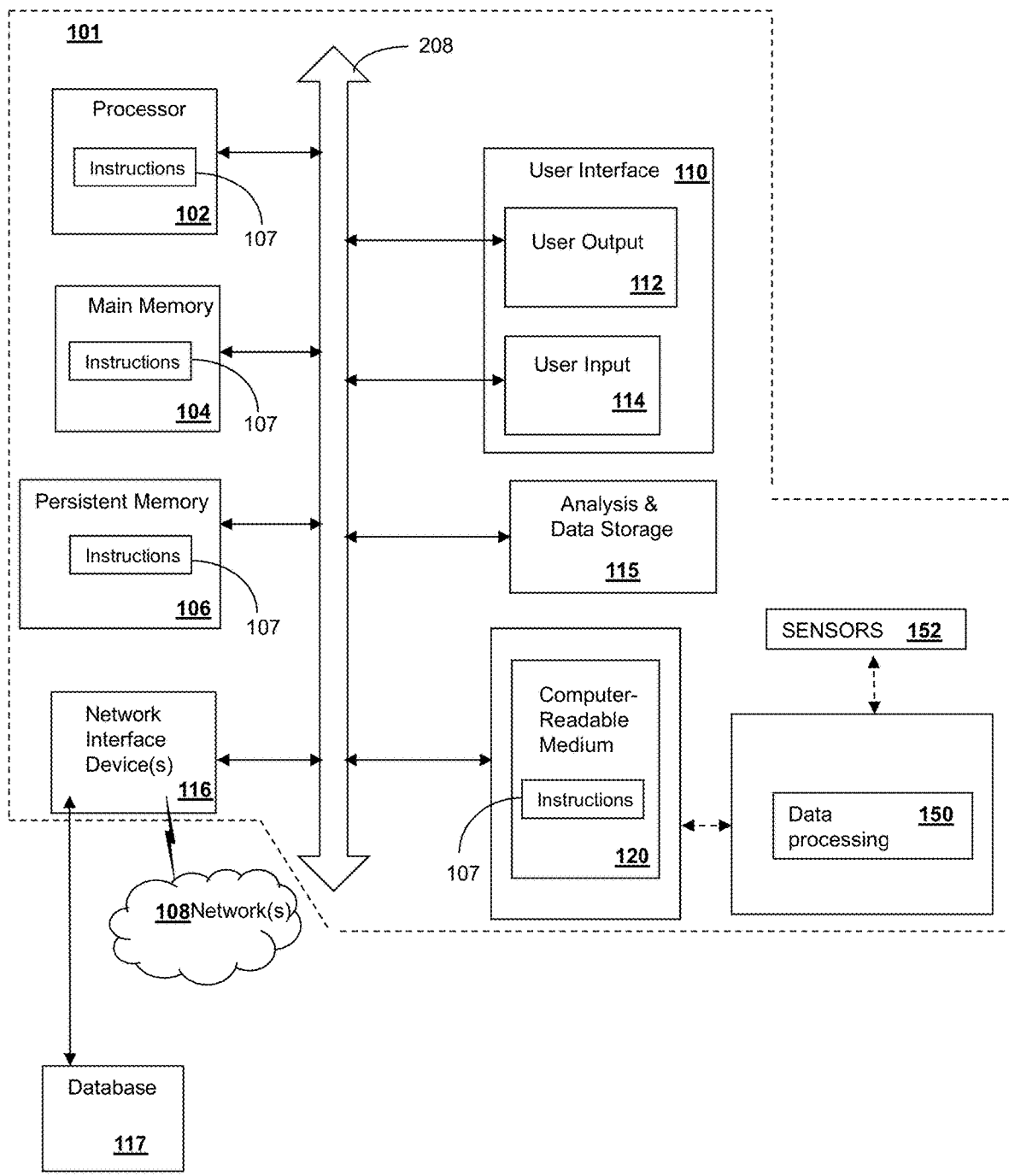
FIG. 6 is a block diagram or a system or apparatus in accordance with the embodiments.

As shown in FIG. 6, an information processing system 101 of a system 200 can be communicatively coupled with the data processing module 150 and a group of client or other devices, or coupled to a presentation device for display at any location at a terminal or server location. According to this example, at least one processor 102, responsive to executing instructions 107, performs operations to communicate with the processing module 150 via a bus architecture 208, as shown. The at least one processor 102 is communicatively coupled with main memory 104, persistent memory 106, and a computer readable medium 120. The processor 102 is communicatively coupled with an Analysis & Data Storage 115 that, according to various implementations, can maintain stored information used by, for example, the data processing module 150 and more generally used by the information processing system 200. The data processing module 150 can be coupled to one or more sensors 152 as needed. Such sensors can be cameras, infrared cameras, motion detectors, barcode scanners, fingerprint readers, proximity sensors, microphones, pressure sensors, temperature sensors, particulate sensors, video cameras, location sensors, and other devices as contemplated herein. Optionally, this stored information can be received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The data processing module 150, and the information processing system 200, can use the information from the history log such as in the analysis process and in making decisions related to measurements taken at a particular environment according to a database of best practices for a particular procedure or procedures.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

The information processing system 200 includes a user interface (or interfaces) 110 that comprises a user output interface 112 and user input interface 114. Examples of elements of the user output interface 112 can include a display, a speaker, one or more indicator lights, one or more transducers that generate audible indicators, and a haptic signal generator or any of the interfaces illustrated or discussed with respect to the figures or elsewhere in the application. Examples of elements of the user input interface 114 can include a keyboard, a keypad, a mouse, a track pad, a touch screen, a touch pad, a microphone that receives audio signals, a camera, a video camera, a CT-Scanner, or any other scanner that scans images. Some user inputs can be sensors or vice-versa. The received audio signals or scanned images, for example, can be converted to electronic digital representations and stored in memory, and optionally can be used with corresponding voice or image recognition software executed by the processor 102 to receive user input data and commands, or to receive test data for example. The voice recognition software can be used to enter or check off items on a checklist and further provide data or text entry allowing the user to enter notes as needed.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can intercommunicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present disclosure. The network interface device 116 can provide a communication interface for the information processing system 100 to access the at least one database 117 according to various embodiments of the disclosure.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

FIGS. 1A-E and 2-4 illustrate examples of systems, methods or process flows, according to various embodiments of the present disclosure, which can operate in conjunction with the information processing system 200 of FIG. 6.

Accordingly, an environment, such as a school classroom or cafeteria can use the system 10 as described herein to safely and, effectively eliminate pathogens in the presence of humans. If power savings or exposure is somehow a concern in a particular environment, the system 10 can further be used with sensors such as motion detectors or infrared cameras or other sensor and/or use timers to provide additional benefits and safety.

It was not until the world witnessed lives lost, loved ones forgotten, and economies destroyed that the imperative gravity of the spread of SARS-CoV-2 was realized. Realizing the exigent demands that a new, invisible viral enemy brings, the development of a infrastructure-based, financially viable solution to battle against the spread of pathogens has inspired the development of the disclosed embodiments herein so that not only children can safely return to the classroom, but further allow the workforce to return to the physical workplace.

What is claimed is:

1. A system for removing airborne pathogens in the form of an LED lighting fixture, comprising:
    a housing having at least one or more chambers;
    a bipolar ionizer residing in the at least one or more chambers;
    at least one particle filter residing in the at least one or more chambers;
    an ultra violet light radiation source residing in the at least one or more chambers;
    a ventilation system that draws in surrounding air at an intake and directs the surrounding air towards the at least one particle filter, the bipolar ionizer, and the ultra violet light radiation source before the ventilation system expels the surrounding air drawn through the intake through an exhaust vent; and
    wherein a structure of the LED lighting fixture includes the housing having a top cover, a directional airflow frame, an LED light panel, and a lower frame and where a portion of the structure itself is coated with a photo-catalyst material to form a treatment chamber where air is treated by the ultra violet light radiation source and the photo-catalyst material within the treatment chamber.

2. The system of claim 1, wherein the bipolar ionizer is of high voltage and low amperage sufficient to rip apart airborne pathogens including viruses and bacteria.

3. The system of claim 1, wherein the system further includes a central access hole where treated air is drawn out of the treatment chamber underneath the directional airflow frame and expelled out of at least the exhaust vent.

4. The system of claim 1, wherein the at least one particle filter further includes a nano-coating of titanium oxide.

5. The system of claim 1, wherein ultra violet light radiation source includes a source of at least one or more of UV-A, UV-B, or UV-C radiation and wherein the housing is configured to keep the one or more of UV-A, UV-B, or UV-C radiation limited to an internal portion of the housing and thereby preventing mammalian exposure external to the housing.

6. The system of claim 1, wherein the at least one particle filter residing in the at least one or more chambers comprises a first particle filter adjacent to the bipolar ionizer and at least a second particle filter adjacent to the exhaust vent.

7. The system of claim 1, wherein the ventilation system comprises a centrifugal fan.

8. The system of claim 1, wherein the system further comprises a machine learning element in communication with one or more sensors among a camera, a video monitoring device, an audio device, a temperature sensor, a pressure sensor, or a particulate sensor to automatically learn and improve operation of the system.

9. The system of claim 1, wherein the at least one chamber having the UV light source further comprises reflective materials that helps to diffuse the UV light source within the at least one chamber.

10. The system of claim 1, wherein the at least one particle filter is treated with a photo catalyst that is continuously energized by a UV-A, UV-B, or UV-C light source that forms part of the ultra violet light radiation source that causes anti-microbial activity.

11. The system of claim 1, wherein the system further comprises a communications link for remotely monitoring one or more sensors including at least an infrared camera or a motion detector operatively coupled to the system.

12. An LED lighting fixture including a system for removing airborne pathogens, comprising:
    a housing having a top cover, a directional airflow frame, and a lower frame and where a portion of the housing itself is coated with a photo-catalyst material to form a treatment chamber;
    a bipolar ionizer residing in the housing;
    at least a first particle filter residing in the proximity of the bipolar ionizer within the housing;
    an ultra violet light radiation source residing in the proximity of the first particle filter within the housing, wherein air is treated by the ultra violet radiation source and the photo-catalyst material within the treatment chamber; and
    a ventilation system that draws in at an intake surrounding air surrounding the LED lighting fixture and directing the surrounding air towards the at least the first particle filter, the bipolar ionizer, and by the ultra violet light radiation source and the treatment chamber before expelling the surrounding air drawn through the intake through an exhaust vent.

13. The LED lighting fixture of claim 12, wherein the first particle filter further includes a coating of titanium oxide or other photo-catalyst material that reacts to exposure to ultraviolet radiation source.

14. The LED lighting fixture of claim 12, wherein ultra violet light radiation source includes a source of UV-A radiation and wherein the housing is configured to keep the UV-A radiation limited to an internal portion of the housing and thereby preventing external exposure of UV-A radiation outside the housing.

15. The LED lighting fixture of claim 12, wherein the system further comprises a communications link for remotely monitoring one or more sensors including a particulate sensor.

16. The LED lighting fixture of claim 12, wherein an area encompassed by the directional airflow frame, and the lower frame forms the treatment chamber where air is treated by the UV light radiation source and a photo-catalyst material that is nano-coated within the treatment chamber.

17. An LED lighting fixture including a system for removing airborne pathogens, comprising:
    a housing having an intake where surrounding air is drawn in and an exhaust vent where the surrounding air that is drawn in is drawn out, a top cover, a directional airflow frame, and a lower frame and where a portion of the housing itself is coated with a photo-catalyst material to form a treatment chamber;

a bipolar ionizer residing in the housing;

at least a first particle filter residing in the proximity of the bipolar ionizer within the housing;

an ultra violet light radiation source residing in the proximity of the first particle filter within the housing; and at least one fan for drawing in at the intake surrounding air surrounding the LED lighting fixture and directing the drawn in surrounding air towards the first particle filter, the bipolar ionizer, and by the ultra violet light radiation source and treating the drawn in surrounding air with the ultraviolet radiation source and the photo-catalyst material within the treatment chamber before expelling the drawn in surrounding air through the exhaust vent.

18. The LED lighting fixture of claim 17, wherein the first particle filter is treated with a photo catalyst in a form of a titanium dioxide nano-coating that is continuously energized by the ultra violet radiation source having a wavelength of 254 nm.

19. The LED lighting fixture of claim 17, wherein the LED lighting fixture further comprises at least a second particle filter residing in the proximity of the ultra violet radiation source within the housing and wherein the second particle filter is treated with a photo catalyst in a form of a titanium dioxide nano-coating that is continuously energized by the ultra violet radiation source.

20. The LED lighting fixture of claim 17, wherein the first particle filter and a second particle filter are treated with a titanium dioxide nano-coating that is continuously energized by the ultra violet radiation source.

\* \* \* \* \*